United States Patent [19]

Lemoine et al.

[11] Patent Number: 4,485,111
[45] Date of Patent: Nov. 27, 1984

[54] DERIVATIVES OF 3-AMINO-1-BENZOFURANYLOXY-2-PROPANOL USEFUL AS CARDIOSELECTIVE BETA-BLOCKING AGENTS

[75] Inventors: Jean Lemoine, Garches; Jean-Pierre Riffaud, Versailles, both of France

[73] Assignee: Laboratories Debat, Paris, France

[21] Appl. No.: 437,210

[22] Filed: Oct. 28, 1982

[30] Foreign Application Priority Data

Oct. 30, 1981 [FR] France ................... 81 20471

[51] Int. Cl.$^3$ .................... C07D 307/80; A61K 31/34
[52] U.S. Cl. ..................................... 424/285; 549/468
[58] Field of Search ......................... 549/468; 424/285

[56] References Cited

U.S. PATENT DOCUMENTS 3,853,923  12/1974  Ito et al. ............................... 549/468

FOREIGN PATENT DOCUMENTS 4057M  4/1966  France .
1503510  10/1967  France .
2137901  12/1972  France .

Primary Examiner—John M. Ford
Assistant Examiner—Bernard I. Dentz
Attorney, Agent, or Firm—Fraser, Barker, Purdue & Clemens

[57] ABSTRACT

The present invention relates, as new industrial products, to (±)-, (+)- and (−)-2,4-diacetyl-5-(3-alkyl-amino-2-hydroxy-propyloxy)-benzofurans of general formula:

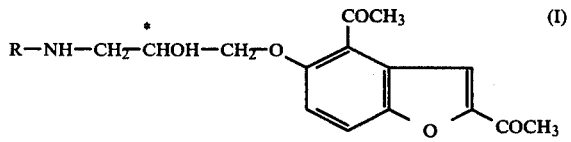

where R is $CH(CH_3)_2$ or $C(CH_3)_3$, and to their acid addition salts. These products are useful in therapeutics, particularly as cardioselective beta-blocking agents.

4 Claims, No Drawings

DERIVATIVES OF 3-AMINO-1-BENZOFURANYLOXY-2-PROPANOL USEFUL AS CARDIOSELECTIVE BETA-BLOCKING AGENTS

The present invention relates, as industrial products, to new derivatives belonging to the family of 3-amino-1-heteroaryloxy-2-propanols, namely derivatives of the 2,4-diacetyl-5-(3-alkylamino-2-hydroxy-propyloxy)benzofuran type. It also relates to the use of these new derivatives in therapeutics and to the method for preparing same.

Substances belonging to the 3-amino-1-aryloxy-2-propanols and 3-amino-1-heteroaryloxy-2-propanols are known to have been recommended as beta adrenergic blocking agents, or beta blockers. In particular, it is known that propanolol (or 3-isopropylamino-1-α-naphthyloxy-2-propanol), which is known particularly from French Pat. Nos. 1 503 510 and 4 057 M, is an excellent reference beta blocker acting simultaneously on the $\beta_1$ receptors (cardiac receptors) and $\beta_2$ receptors (bronchial receptors). It is also known that the derivatives of benzofuran according to French patent No. 72-17290 (Publication No. 2 137 901), which are monoacetylated and not diacetylated like those of the invention, have beta-blocking properties which are not cardioselective. It has been surprisingly found that the new derivatives according to the invention, which are structurally different from the heretofore known products, present the advantage of being cardioselective beta-blocking agents in that they act on the $\beta_1$ receptors and have no effect on the $\beta_2$ receptors.

The new derivatives according to the invention which belong to the family of 3-amino-1-heteroaryloxy-2-propanols are characterized in that they are selected from the group consisting of:

(i) the (±)-, (+)- and (−)-2,4-diacetyl-5-(3-alkylamino-2-hydroxy-propyloxy)-benzofurans of the general formula:

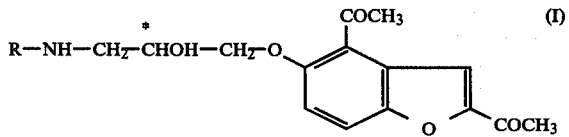

(where R represents an isopropyl or tert-butyl group), and (ii) the acid addition salts thereof.

The invention therefore covers the (±) racemics of formula as well as the optical (+) and (−) isomers.

Among the inorganic and organic acids which are suitable for salifying the free bases of formula 1, particular mention may be made of hydrochloric, maleic, fumaric, aspartic and paratoluenesulfonic acids.

The compounds of formula 1 may be prepared according to a method known per se by application of conventional reaction mechanisms. The method which is recommended according to the invention is schematized in diagram I hereinbelow.

This method comprises, successively:

(a) the reaction of the 2,4-diacetyl-5-hydroxybenzofuran II [prepared as indicated by Jean-Marc Clavel et al., Bull. Soc. Chim., 1976, pages 131-134] with a halogenated epoxide of formula III (where Hal is Cl or Br, the preferred halogen being bromine), to obtain 2,4-diacetyl-5-(2,3-epoxy-propyloxy)-benzofuran IV; and (b) the reaction of compound IV thus obtained with an amine NH$_2$R (where R is isopropyl or tert-butyl) to obtain a compound of formula I

DIAGRAM I

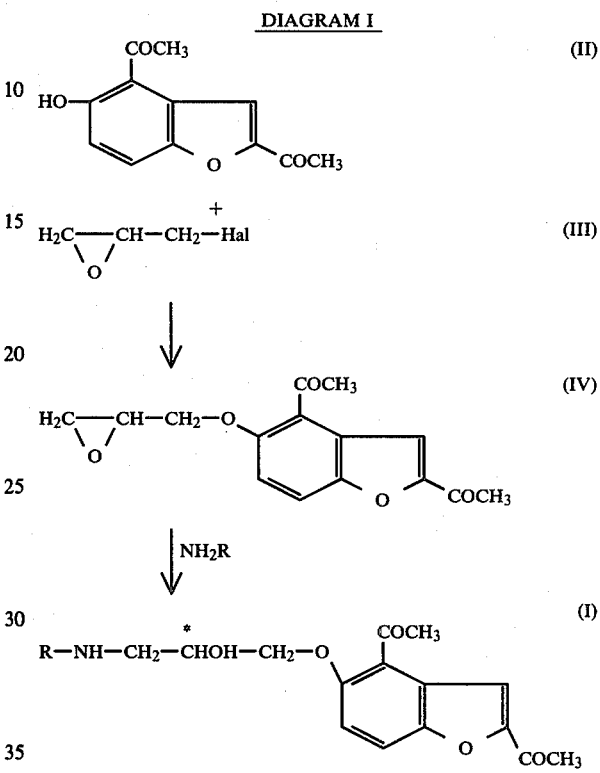

The best mode for carrying out this method consists in reacting:

in step (a) 1.2 to 1.8 moles of III with 1 mole of II in a ketone having from 3 to 6 C atoms (particularly acetone, 2-butanone, 2-pentanone, 3-pentanone), in the presence of a compound selected from Li, Na, K, Na$_2$CO$_3$ and K$_2$CO$_3$, at reflux for at least 4 hours; and in steb (b) 1.5 to 2.2 moles of NH$_2$R with 1 mole of IV, in a lower alkanol having from 1 to 3 C atoms, at reflux for at least 2 hours.

The enantiomers of formula I may be resolved from the racemic according to a method known per se.

The products according to the invention are cardioselective beta-blocking agents in that they act on the $\beta_1$ receptors without having any effect on the $\beta_2$ receptors. By reason of their antiarrythmic, antihypertensive and antianginal properties, they are indicated in the treatment of cardiovascular diseases such as hypertension in particular, the reduction or prevention of disorders of the rhythm, the prophylaxis of angina pectoris and the cardiovascular manifestations of hyperthyroidism.

According to the invention, a therapeutic composition is recommended which is characterized in that it contains, in association with a physiologically acceptable excipient, at lest one compound of formula I or one of its acid addition salts.

Other advantages and features of the invention will be more readily understood on reading the following description of examples of preparation which are in no way limiting but given by way of illustration.

PREPARATION I

Obtaining of the hydrochloride of
(±)-2,4-diacetyl-5-(3-tert-butylamino-2-hydroxy-propyloxy)-benzofuran (Example 1; Code No. R 7262)

(a) 2,4-diacetyl-5-(2,3-epoxy-propyloxy)-benzofuran

In a flask, a suspension of 10 g (0.046 mole) of 2,4-diacetyl-5-hydroxybenzofuran, of 9.5 g (0.069 mole) of dry $K_2CO_3$ and of 9.45 g (0.069 mole) of epibromohydrin in 100 ml of previously dried 2-butanone, is maintained at reflux for 8 hours and with stirring. The mineral salts (KBr formed and $K_2CO_3$ remaining) are eliminated by filtration after having been rinsed with acetone. The resultant filtrate is evaporated to dryness, and the residue of evaporation is taken up in chloroform. The chloroform phase thus obtained is washed in water and dried over $MgSO_4$. The chloroform is eliminated by evaporation to dryness. By recrystallization of the residue of evaporation from a benzene-cyclohexane (1:1) v/v mixture, 11.8 g (yield: 93%) of the expected product are obtained, m.p.=114° C.

(b) (±)-2,4-diacetyl-5-(3-tert-butylamino-2-hydroxy-propyloxy)-benzofuran 10.5 g (0.0383 mole) of 2,4-diacetyl-5-(2,3-epoxy-propyloxy)-benzofuran, 5.6 g (0.0767 mole) of tertiobutylamine and 100 ml of ethanol are mixed in a flask. This mixture is taken to reflux for 4 hours. The ethanol is then evaporated. By recrystallization from a toluene-cyclohexane (1:1) v/v mixture at −30° C., 9 g (yield: 70%) of the expected product are obtained, m.p.=122° C.

(c) Hydrochloride of (±)-2,4-diacetyl-5-(3-tert-butylamino-2-hydroxy-propyloxy)-benzofuran 8.9 g of (±)-2,4-diacetyl-5-(3-tert-butylamino-2-hydroxy-propyloxy)-benzofuran in solution in $CHCl_3$ are charged in a reactor cooled externally with an ice bath, then a stream of gaseous HCl is bubbled up to saturation. After evaporation of $CHCl_3$ under reduced pressure, a precipitate is obtained which is taken up in $CHCl_3$, triturated drained and dried. 9.2 g of the expected product are obtained, m.p.=214°-216° C.

PREPARATION II

Obtaining of the hydrochloride of
(±)-2,4-diacetyl-5-(3-isopropyl-amino-2-hydroxy-propyloxy)-benzofuran (Example 2)

By proceeding as indicated in preparation I, but by replacing the tert-butylamine by isopropylamine in step b), the hydrochloride of (±)-2,4-diacetyl-5-(3-isopropylamino-2-hydroxy-propyloxy)-benzofuran is obtained.

Part of the results of the tests run in animals, particularly with the preferred product according to the invention, namely R 7262 (Example 1), has been summarized hereinbelow.

TOXICITY

The LD-50 of the product of Example 1 is, by the oral route, higher than 500 mg/kg in the mouse.

As regards the LD-0 (maximum non-lethal dose) in the guinea pig by the intravenous route, Table I hereinbelow shows that the product of Example 1 is less toxic than propanolol.

TABLE I

| Product | Code No. | LD-0 iv guinea pig mg/kg |
|---|---|---|
| Example 1 | R 7262 | 48.3 |
| Propanolol | — | 26.1 |

Study of the beta-blocking properties in vivo in the guinea pig (a) Study at cardiac level Tricoloured male guinea pigs with an average weight of 400 to 500 g, are anaesthetized with ethyl-urethane (1.5 g/kg, ip route). The cardiac rhythm is recorded from the pulsatile signal of the arterial pressure picked up at the left carotid.

After a period of stabilisation of 30 minutes, the tachycardia-inducing effect is determined by an i.v. injection of isoprenaline at 0.25 µg/kg before then 15, 30, 45 and 60 minutes after the injection of the beta-blocker to be studied or its solvent. This effect is expressed by the cardiac rhythm attained with respect to the initial rhythm. The results are shown in Table II hereinbelow.

(b) Study at bronchial level

The study on the bronchial $\beta_2$ receptors was made on the animals used for the cardiac study, at the same time as said study.

The $\beta_2$-blocking effect of the substances to be studied was sought according to the method described by LINEE et al (1974) from the technique of KONZETT and ROESSLER (1940). To this end, the variation, provoked by the administration of isoprenaline and the beta-blockers to be studied, of the amplitude of the bronchospasm induced by serotonin was measured. Here, the isoprenaline was introduced 30 seconds before the i.v. injection of serotonin then the amplitude of the bronchospasm was measured before then 15, 30, 45 and 60 minutes after the injection of the beta-blocker to be studied or its solvent. The results are shown in Table III hereinbelow.

The results of Tables II and III show that the R 7262 is a cardio-selective beta-blocking agent.

TABLE II

Blocking effect on the cardiac $\beta_1$ receptors

| | | | | Cardiac rhythm provoked by injection of isoprenaline | | | | |
|---|---|---|---|---|---|---|---|---|
| | Number of animals treated | dose mg/kg | Initial cardiac rhythm | before administration of beta-blocker | After administration (time in minutes) of beta-blocker | | | |
| Product | | | | | 15 min | 30 min | 45 min | 60 min |
| (controls) | 10 | — | 227 ± 17 | 268 ± 21 | 257 ± 17 | 251 ± 18 | 245 ± 18 | 240 ± 17 |
| Propanolol | 6 | 0.0625 | 262 ± 44 | 289 ± 39 | 255 ± 49 | 269 ± 48 | 272 ± 48 | 274 ± 51 |
| Propanolol | 6 | 0.25 | 202 ± 28 | 257 ± 36 | 209 ± 35 | 228 ± 45 | 231 ± 49 | 232 ± 48 |
| Example 1 (R 7262) | 7 | 0.0625 | 245 ± 33 | 293 ± 28 | 266 ± 22 | 275 ± 24 | 283 ± 22 | 285 ± 20 |
| Example 1 (R 7262) | 7 | 0.25 | 223 ± 45 | 257 ± 36 | 217 ± 48 | 228 ± 51 | 237 ± 51 | 241 ± 51 |

Note
The results are expressed in the form: "Mean ± Standard Error to Mean"

TABLE III

Blocking effect on the bronchial $\beta_2$ receptors

| | Number of animals treated | Dose mg/kg | AMPLITUDE OF BRONCHOSPASM* | | | | |
|---|---|---|---|---|---|---|---|
| | | | Before beta-blocking product | After beta-blocking product | | | |
| Product | | | | 15 min | 30 min | 45 min | 60 min |
| (controls) | 10 | — | 74 ± 11 | 62 ± 13 | 57 ± 12 | 69 ± 11 | 68 ± 13 |
| Propanolol | 6 | 0.0625 | 79 ± 9 | 8 ± 5 | 12 ± 8 | 16 ± 8 | 22 ± 8 |
| Propanolol | 6 | 0.25 | 88 ± 5 | 2 ± 1 | 3 ± 1 | 3 ± 1 | 7 ± 3 |
| Ex 1 (R 7262) | 7 | 0.0625 | 76 ± 9 | 58 ± 13 | 54 ± 10 | 43 ± 11 | 54 ± 13 |
| Ex 1 (R 7262) | 7 | 0.25 | 72 ± 11 | 58 ± 10 | 45 ± 11 | 45 ± 13 | 51 ± 11 |

Note
*The amplitude of the bronchospasm is expressed in % with respect to the amplitude of the bronchospasm induced by serotonin; the results are given here in the form: "Mean ± Standard Error to Mean"

Study of the beta-blocking properties in the anaesthetized dog

Mongrel dogs, of either sex, weighing from 13 to 30 kg were used. Anaesthesia is induced by i.p. injection of Nembutal (25 mg/kg) and maintained by a perfusion of Nembutal (25 mg/kg at the rate of 0.2 ml/min.). The trachea is intubated and the animal is given respiratory assistance (respirator of the "BIRD MARK 8" type). The carotid arterial pressure is measured by a pressure sensor (of the "NARCO P 1000 B" type). After thoracotomy, the left ventricular pressure is measured by means of a sensor of the same type. The cardiac rhythm is recorded, from the signal of the carotid pressure, by a cardiotachometer ("NARCO type 7302"). The rate of increase in the isometric tension of the left ventricle (dP/dt) was assessed by a differentiator coupler ("NARCO type 7301").

After i.v. injection of atropine (2 mg/kg) and a period of stabilisation of 30 minutes, the curves showing dose-effect of isoprenaline, for each of the parameters, were sought. There was a 5 minute interval between the injections of each dose of isoprenaline. After a period of 10 minutes, the animals receive the first dose of beta-blocker then 10 minutes after the series of doses of isoprenaline. Again, after 10 minutes, the injection of the second dose of isoprenaline is made. This experimental sequence is repeated until each animal has received 3 to 4 doses of beta-blocker.

The antagonism of the effects of isoprenaline is assessed by calculating the $pA_{10}$ which is the dose of antagonist, in mg/kg, in the presence of which the doses of isoprenaline must be multiplied by 10 (dose ratio 10) to have the same effect as in the absence of antagonist. The $pA_{10}$ has been calculated by extrapolation of the log $(R \times D^{-1}) = f(PA_X)$ curve where $R \times D^{-1}$ is the ratio of the equiactive doses of isoprenaline.

The effects of the isoprenaline were measured with respect to the basic values taken just before the beginning of each new range of isoprenaline as regards the cardiac frequency and the dP/dt. For the diastolic arterial pressure, by reason of the marked hypotensive activity of the R 7262, the effects of the isoprenaline were assessed with respect to the initial value, taken before any injection.

The results are shown in Table IV.

TABLE IV

Beta-blocking effect in the anaesthetized dog

| Product (number of animals) | Cardiac frequency | | Diastolic A.P.* | | dP/dt | |
|---|---|---|---|---|---|---|
| | $pA_{10}$ | slope | $pA_{10}$ | slope | $pA_{10}$ | slope |
| R 7262 (n = 5) | 0.23 | 0.7 | 3 | — | 0.10 | 0.9 |
| Propanolol (n = 5) | 0.24 | 1.1 | 0.1 | — | 0.13 | 0.8 |

Note:
*i.e. Diastolic Arterial Pressure
— means "not measured"

It is observed, from the results of Table IV, that, in the anaesthetized dog, the R 7262 antagonizes the effects of isoprenaline at the level of the $\beta_1$ receptors: chronotropic and inotropic action positive. On the other hand, the R 7262 has no activity with respect to the $\beta_2$ effects of isoprenaline which are here illustrated by the hypotensive action. Therefore, R 7262 is cardioselective, unlike propanolol.

What is claimed is:

1. A derivative belonging to the family of 3-amino-1-heteroaryloxy-2-propanols, which is selected from the group consisting of:

(i) a (±)-, (+)- and (−)2,4-diacetyl-5-(3-alkyl-amino-2-hydroxypropyloxy)-benzofuran having the formula:

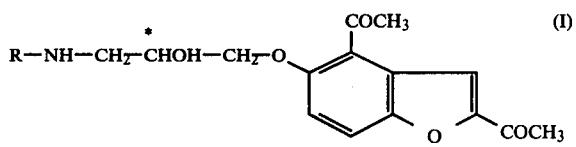

(wherein R represents an isopropyl or tert-butyl group), and (ii) the pharmaceutically effective acid addition salts thereof.

2. (±)-2,4-Diacetyl-5-(3-tert-butylamino-2-hydroxypropyloxy)-benzofuran and its pharmaceutically effective acid addition salts.

3. (±)-2,4-Diacetyl-5-(3-isopropylamino-2-hydroxypropyloxy)-benzofuran and its pharmaceutically effective acid addition salts.

4. A therapeutical composition for the treatment of arrythmia of the heart, angina pectoris, hypertension and the cardiovascular manifestations of hypertension which contains, in association with a physiologically acceptable excipient, an effective amount of at least one compound of any one of claims 1 to 3.